United States Patent [19]

Arnold et al.

[11] Patent Number: 5,442,032

[45] Date of Patent: Aug. 15, 1995

[54] COPOLYMERS OF 1,4-DIOXEPAN-2-ONE AND 1,5,8,12-TETRAOXACYCLOTETRADECANE-7-14-DIONE

[75] Inventors: Steven C. Arnold, Sparta; Rao S. Bezwada, Whitehouse Station; Alastair W. Hunter, Bridgewater, all of N.J.

[73] Assignee: Ethicon, Inc., Somerville, N.J.

[21] Appl. No.: 213,787

[22] Filed: Mar. 15, 1994

[51] Int. Cl.$^6$ .................... C08G 63/08; C08G 63/676; A61L 17/00

[52] U.S. Cl. .................... 528/354; 428/357; 428/394; 428/395; 428/480; 525/411; 525/415; 525/450; 528/361; 606/228; 606/230; 606/231

[58] Field of Search ............... 428/357, 394, 395, 480; 525/411, 415, 450; 528/354, 361; 606/228, 230, 231

[56] References Cited

U.S. PATENT DOCUMENTS

| | | | |
|---|---|---|---|
| 4,052,988 | 10/1977 | Doddi et al. | 128/335.5 |
| 4,190,720 | 2/1980 | Shalaby | 528/354 |
| 4,470,416 | 9/1984 | Kafrawy | 128/335.5 |
| 5,080,665 | 1/1992 | Jarrett et al. | 606/219 |

FOREIGN PATENT DOCUMENTS 0460428 12/1991 European Pat. Off. .

OTHER PUBLICATIONS

Synthesis of Polylactides, Polyglycolides and Their Copolymers, Jan Neiuwenhuis, Clinical Materials 0267 10 (1992) pp. 59–67;
Determination of the Conformation of 1,4-Diheterocyclanes. Annikki Partanen and Pertti Ayras, Finn. Chem. Lett (1977) pp. 208–212.
Polymerization of 1,5-Dioxepan-2-One. 1. Synthesis and Characterization of the Monomer 1,5-Dioxepan-2-one and Its Cyclic Dimer 1,5,8,12-Tetraoxacyclotetradecane-2,9-dione, Torbjorn Mathisen and Ann-Christine Albertsson, American Chemical Society (1989) pp. 3838–3842.
Polymerization of 1,5-Dioxepan-2-one. 2. Polymerization of 1,5-Dioxepan-2-one and Its Cyclic Dimer, Including a New Procedure for the Synthesis of 1,5-Dioxepan-2-one, Torbjorn Mathisen, Kristina Masus, and Ann-Christine Albertson, American Chemical Society (1989) pp. 3842–3846.
A New Synthesis of 1,5-Dioxepan-2-One. A. Kafrawy, F. V. Mattei, and S. W. Shalaby, Journal of Polymer Science, vol. 25, (1987) pp. 2629–2630.
Cyclization during Polyesterification: Isolation of an 18-Member Ring Compound from Reaction of Phthalic Anhydride with 2,2-Dimethyl-1-2,Propanediol Gang-Fung Chen and Frank N. Jones, Journal of Applied Polymer Science, vol. 41 (1990) pp. 2517–2520.
Copolymers of 1,5-Dioxepan-2-One and L-or D.L-Dilactide-Synthesis and Characterization. Ann-Christine Albertsson and Anders Lofgren, Makromol. Chem., Marcromol. Symp. 53, (1992) pp. 221–131.

*Primary Examiner*—Melvyn I. Marquis
*Assistant Examiner*—Shelley A. Dodson
*Attorney, Agent, or Firm*—Hal Brent Woodrow

[57] ABSTRACT

This invention provides various copolymers comprising a repeating unit of the chemical formula:

$$(CH_2CH_2CH_2OCH_2CO_2)$$

and other repeating units having a chemical formula selected from the group consisting of:

$$(CHRCO_2),$$

$$([CH_2]_5CO_2),$$

$$(CH_2CH_2OCH_2CO_2),$$

$$(CH_2CH_2CH_2OCO_2), \text{ and}$$

combinations of two or mope thereof wherein R is a hydrogen atom or a methyl group and the first repeating unit is less than 45 weight percent of the total weight of the copolymer. This invention also relates to use of these copolymers in the fabrication of absorbable surgical devices such as sutures and as coatings for medical devices.

26 Claims, No Drawings

COPOLYMERS OF 1,4-DIOXEPAN-2-ONE AND 1,5,8,12-TETRAOXACYCLOTETRADECANE-7-14-DIONE

FIELD OF THE INVENTION

This invention relates to copolymers derived from 1,4-dioxepan-2-one and its cyclic dimer, 1,5,8,12-tetraoxacyclotetradecane-7-14-dione, and especially to crystalline copolymers having mechanical and biological properties which are desirable for tile preparation of absorbable surgical sutures and devices.

BACKGROUND OF THE INVENTION

Although homopolymers and copolymers of 1,4-dioxepan2-one have been described in the literature, very little is known about the physical properties of these polymers. The first mention of homopolymers of 1,4-dioxepan-2-one was by Spanagel in U.S. Pat. No. 2,163,109 issued on Jun. 20, 1939, which cites a German article authored by Palomaa et al. in *Ber.* 66, 1629, (1933). Spanagel described the synthesis of these homopolymers from hydroxyether acids using a metal catalyst. These homopolymers were depolymerized after synthesis into lactones for use in perfumes. The physical properties of this polymer were not described.

More recently 1,4-dioxepan-2-one homopolymers and copolymers were described by Doddi et al. in U.S. Pat. No. 4,052,988. Doddi described the synthesis of homopolymers and copolymers of 1,4-dioxepan-2-one for use as absorbable synthetic sutures, tendons and the like. The copolymers disclosed by Doddi et al. were described as containing predominately 1,4-dioxepan-2-one and up to 50 weight percent of another copolymerizable monomer such as lactide or glycolide.

Similarly, European Patent Application, EPA 460,428 A2, also describes copolymers of 1,4-dioxepan-2-one and other fast reacting monomers such as glycolide and lactide. This application describes a block copolymer formed by a two stage polymerization process. In the first stage of this process, a prepolymer is formed containing predominately a monomer such as 1,4-dioxepan-2-one, the remainder of the prepolymer being a monomer such as glycolide or lactide. In the second stage of the polymerization, the prepolymer is reacted with an additional lactone monomer to provide a segmented block copolymer. Unfortunately, neither Doddi or EPA 460 428 A2 describes the physical properties of polymers containing 1,4-dioxepan-2-one.

The structural isomer of 1,4-dioxepan-2-one, namely 1,5-dioxepan-2-one, has also been studied. U.S. Pat. Nos. 4,190,720 and 4,470,416 describe copolymers of 1,5-dioxepan-2-one and ε-caprolactone, glycolide, or lactide. In addition, the homopolymerization of 1,5-dioxepan-2-one and its cyclic dimer has been investigated. Albersson et al. (*Macromolecules* 22, 3838–3846, 1989) have polymerized 1,5-dioxepan-2-one and its cyclic dimer. The resulting poly[1,5-dioxepan-2-one]was completely amorphous with a glass transition temperature of −39° C. Since poly[1,5-dioxepan-2-one]is an amorphous elastomer, it can only be used as an absorbable toughening agent either as a discreet phase in a polymer blend or composite, or as a segment in a block copolymer.

Surprisingly, we have discovered that poly[1,4-dioxepan-2-one]is a semicrystalline polymer. In addition, contrary to the teachings of Doddi, poly[1,4-dioxepan-2one]crystallizes too slowly to be melt spun into fibers. Due to the slow crystallization rates of poly[1,4-dioxepan-2-one], it is desirable to limit the amount of 1,4-dioxepan-2-one that is incorporated into copolymers to less than 45 weight percent. However, poly[1,4-dioxepan-2-one]unlike the amorphous poly[1,5-dioxepan-2-one]be used in biomedical applications that require greater dimensional stability (such as molded parts or sutures). When poly[1,4-dioxepan-2-one]is employed in a polymer blend or composite, it would exist as a discreet crystalline phase; in a block copolymer, it would also exist as a discreet crystallizable segment that would tend to phase separate and crystallize into distinct phases. These copolymers, blends, or composites would be composed of at least two crystalline regions; one region being rich in poly[1,4-dioxepan-2-one]. Consequently, polymeric materials which incorporate the crystallizable poly[1,4-dioxepan-2-one]would exhibit new biophysical properties such as breaking strength retention and absorption profiles not achieved with its structural analog.

SUMMARY OF THE INVENTION

In one aspect of this invention we have discovered a copolymer comprising a first repeating unit of the chemical formula:

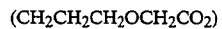

and a second repeating unit having a chemical formula selected from the group consisting of:

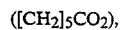

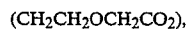

combinations of two or more thereof wherein R is a hydrogen atom or a methyl group and the first repeating unit is less than 45 weight percent of the total weight of the copolymer wherein the copolymer is selected from the group consisting of: a) a copolymer comprising the reaction product of a prepolymer of the first repeating unit and the remainder of the copolymer being the second repeating unit; b) a random copolymer comprising the first repeating unit and the second repeating unit; c) a copolymer comprising the reaction product of a prepolymer containing the second repeating unit and the remainder of the copolymer being the first repeating unit; d) a copolymer comprising the reaction product of a prepolymer containing less than 45 weight percent of the first repeating unit and greater than 55 weight percent of the second repeating unit in the prepolymer and the remainder of the copolymer being the second repeating unit.

The copolymer of this invention can be readily melt spun using conventional techniques. The fibers prepared from these copolymers have the combination of mechanical and biological properties necessary for use as an absorbable monofilament surgical suture. By varying the ratio of lactide, glycolide, ε-caprolactone, trimethylene carbonate and 1,4-dioxanone to 1,4-dioxepan-2-one in the copolymer, or by varying the concentration of prepolymer in the copolymer, the compliance and the in vivo breaking strength retention and absorption profiles can be modified significantly. Therefore, the properties of the copolymers of this invention can be tailored for specific applications.

The copolymers are useful for the preparation of surgical devices such as surgical filaments, especially absorbable monofilament surgical sutures, although these copolymers may find use in the fabrication of surgical devices. For example, the copolymers may be used as orthopedic pins, screws, clamps, and plates; surgical knits or woven fabrics (such as medical dressings, hernia patches, gauze, meshes, fabrics, sheets, felts or sponges); surgical staples, hemostatic clips; suture knot clips; hooks; buttons; snaps; bone substitutes (such as vertebral discs and mandible prostheses); vascular implants and the like. The copolymers of this invention may be fashioned into surgical devices by conventional melt processing techniques.

Additionally, the inventive copolymers may also be used as coatings for sutures and the like to improve the knot strengths and the tiedown properties and to reduce the tissue drag of sutures.

DETAILED DESCRIPTION OF THE INVENTION

The copolymers of the present invention are composed of repeating units derived from 1,4-dioxepan-2-one or its cyclic dimer (1,5,8,12-tetraoxacyclotetradecane-7,14-dione) and a second lactone monomer or a mixture of lactone comonomers. Suitable second monomers are defined for the purpose of the present invention to be cyclic esters selected from the group consisting of glycolide, L-lactide, D,L-lactide, $\epsilon$-caprolactone, 1,4-dioxanone, trimethylene carbonate and combinations of two or more thereof. The inventive copolymers will contain less than 45 weight percent of 1,4-dioxepan-2-one repeating units; the remainder of the copolymer will be composed of one or more repeating units derived from the second lactone monomer(s). Preferably, the weight percent of repeating units derived from 1,4-dioxepan-2-one will be in the range of from about 1 weight percent to about 40 weight percent, and most preferably, in the range of from about 5 weight percent to about 30 weight percent.

The copolymers of the present invention may be statistically random copolymers or segmented block copolymers. Statistically random copolymers are prepared by copolymerizing 1,4-dioxepan-2-one or its cyclic dimer with one or more lactone monomers in a one stage polymerization. The use of the cyclic dimer of 1,4-dioxepan-2-one would produce a statistically random copolymer with an initial sequence distribution different from the copolymer formed using the 1,4-dioxepan-2-one. However, since transesterification reactions occur among the copolymer chains, it may be possible to find reaction conditions using the cyclic dimer of 1,4-dioxepan-2-one which would form a copolymer of the same sequence distribution that would be produced using 1,4-dioxepan-2-one. The choice to use 1,4-dioxepan-2-one or its cyclic dimer would depend on the desired copolymer microstructure and its physical properties; in some cases, 1,4-dioxepan-2-one may be the most appropriate monomer to employ; in other cases, its cyclic dimer may be. Preferably, statistically random copolymers of 1,4-dioxepan-2-one and one or more lactone monomers will contain from about 1 weight percent to about 40 weight percent 1,4-dioxepan-2-one repeating units, and most preferably, from about 5 weight percent to about 30 weight percent 1,4-dioxepan-2-one repeating units.

Segmented block copolymers are prepared in a two stage polymerization. In the first stage, a prepolymer is formed. In the second stage, the prepolymer is usually copolymerized with a monomer composition different from the prepolymer. For example, a prepolymer could be formed from a homopolymer of 1,4-dioxepan-2-one or its cyclic dimer and then reacted with one or more lactone monomers. The inherent viscosity of the prepolymer used in the segmented block copolymer may vary from about 0.5 to about 2.5 dL/g as measured in a 0.1 g/dL solution of hexafluoroisopropanol at 25° C. The prepolymer content of the segmented block copolymer can vary; however, as a general guideline, the weight percent of prepolymer will be in the range of from about 1 to about 90 weight percent. Because of transesterification reactions occurring among the polymer chains, these copolymers would have substantially the following chemical structure:

$$(AB)_x$$

wherein A is a block composed primarily of repeating units of the chemical formula:

$$(CH_2CH_2CH_2OCH_2CO_2)$$

and B is a block composed primarily of repeating units having a chemical formula selected from the group consisting of:

$$(CHRCO_2),$$

$$([CH_2]_5CO_2),$$

$$(CH_2CH_2OCH_2CO_2),$$

$$(CH_2CH_2CH_2OCO_2), \text{ and}$$

combinations of two or more thereof wherein R is a hydrogen atom or a methyl group and the first repeating unit is less than 45 weight percent of the total weight of the copolymer. Preferably x will be in the range of from about 1 to about 50 and the number average molecular weight of the segmented block copolymer will be in the range of from about 2,000 to about 120,000 grams/mole. The extent to which the repeating units are scrambled by transesterification reactions will depend on the reaction conditions used in both stages of the polymerization. Some of the reaction variables that would affect the amount of transesterification that occurs include the temperature, the reaction times, the catalyst and its concentration, and the molar ratio of monomer to initiator, i.e., the concentration of chain ends.

In another embodiment of the present invention, the prepolymer may be formed from one or more lactone monomers which may include 1,4-dioxepan-2-one or its cyclic dimer. The resulting prepolymer is then reacted with one or more other lactone monomers which may include 1,4-dioxepan-2-one or its cyclic dimer in a second polymerization. Suitable lactone monomers for copolymerization are selected from a group consisting of glycolide, L-lactide, D,L-lactide, 1,4-dioxan-2-one, $\epsilon$-caprolactone, trimethylene carbonate, 1,4-dioxepan-2-one, 1,5-dioxepan-2-one, and valerolactone. The only compositional requirement is that the copolymer contains 1,4-dioxepan-2-one and the weight percent of repeating units of 1,4-dioxepan-2-one in the segmented block copolymer be less than 45 weight percent overall.

By varying the amounts of 1,4-dioxepan-2-one or its cyclic dimer, the solubility of the prepolymer in the second batch of molten monomers can be adjusted so that the prepolymer dissolves rapidly. In addition, the length of the blocks can be controlled to some extent by the reaction conditions which determine the amount of transesterification that occurs among the copolymer chains, by the weight ratio of the prepolymer to the sum of the monomers in the second stage of the polymerization, by the molecular weight of the prepolymer, and by the catalyst concentration. These factors can be varied to achieve the desired breaking strength retention and absorption profiles of a surgical device made from these copolymers. As a general guideline, the prepolymers may have a inherent viscosity in the range of from about 0.5 to about 2.5 dL/g as measured in a 0.1 g/dL solution of hexafluoroisopropanol at 25° C. The content of prepolymer in the segmented block copolymers may also vary, generally in the range of from about 1 to about 90 weight percent, based on the total weight of the copolymer.

The copolymers of the present invention can be prepared by conventional polymerization techniques well known in the art, for example, as described in U.S. Pat. No. 4,653,497. In the case of the segmented block copolymers, the prepolymer is dissolved in and then reacted with a molten lactone monomer or monomers in the presence of an organometallic catalyst at elevated temperatures. The organometallic catalyst is preferably a tin compound, e.g. stannous octoate, and is present in the monomer mixture at a molar ratio of the sum of all of the monomers to catalyst preferably ranging from 5,000:1 to 80,000:1. The initiator is typically an alkanol, a glycol, a hydroxy acid, or an amine, and is present in the monomer mixture at a molar ratio of the sum of all of the monomers to initiator ranging from 400:1 to 2000:1. The copolymerization can be carried out at a temperature range from 100° C. to 220° C., preferably from 160° C. to 200° C., until the desired copolymer is formed; generally no longer than 16 hours is required. Alternatively, the copolymerization can be carried out in two or more stages at different temperatures. For example, the reaction temperature can be maintained at a certain temperature between 100° C. and 140° C. for a short time period between ten minutes and two hours, perhaps to allow the prepolymer to fully dissolve into a mixture of molten comonomers without too many transesterification reactions occurring, and then, the reaction temperature is increased to a higher temperature between 180° C. and 200° C. for a longer period of time, usually between two hours and forty eight hours. Additionally, these copolymers may also be prepared using solution or suspension polymerization methods as substantially as described by Jan Nieuwenhuis in *Clinical Materials*, vol. 10, 1992 pages 59–67.

One preferred method for preparing copolymers containing repeating units of ($CH_2CH_2CH_2OCH_2CO_2$) is to polymerize the cyclic dimer of 1,4-dioxepan-2-one, isolate the resulting poly[1,4-dioxepan-2-one](PDP), and then react this polymer with another lactone monomer or with a mixture of lactone monomers in the molten state. This two stage process may be carried out as two discreet reactions or as a two step, one pot procedure. For example, the cyclic dimer of 1,4-dioxepan-2-one is melt polymerized at 185° C. using stannous octoate as the Lewis acid catalyst and diethylene glycol as the initiator. The PDP so formed is allowed to stand at room temperature for three days and crystallize into a hard white solid. The PDP may be isolated and used as prepared if the conversion is high enough, or purified by first dissolving it into chloroform and then precipitating the polymer into an excess of methanol. The precipitated polymer is collected by suction filtration and vacuum dried at room temperature. In any case, the PDP is then dissolved in a molten lactone monomer or a molten mixture of lactone monomers usually at a relatively low temperature between 100° C. and 140° C. Lactone monomers such as glycolide, L-lactide, 1,4-dioxan-2-one, ε-caprolactone, or trimethylene carbonate can be used. After the PDP has dissolved completely and a homogeneous solution has been obtained, the reaction temperature is raised to a temperature between 175° C. and 200° C. The only exception to this general procedure is when 1,4-dioxan-2-one is employed in which case the temperature is maintained at 110° C. for the duration of the entire experiment. The reaction times are varied depending upon the desired mechanical properties which are determined in part by the microstructure of segmented block copolymer and by the amount of transesterification that is allowed to occur during the second stage of the synthesis.

In preferred embodiments, the copolymers of this invention have a degree of crystallinity and a molecular weight which render the copolymers suitable for extrusion into fibers or films, or for injection molding into surgical devices such as staples. Advantageously, the crystallinity of the copolymers will be greater than about 10 percent and most preferably above 25 percent as measured by x-ray diffraction, to enable the copolymer to maintain its structural integrity at the elevated temperatures that may be encountered during the shipping and storage of surgical devices. Preferably, the inherent viscosity of the crystalline copolymers will range from about 0.8 to about 4.0, more preferably from about 1.2 to about 2.0 dL/g in a 0.1 g/dL solution of hexafluoroisopropyl alcohol (HFIP) at 25° C. A copolymer with an inherent viscosity below about 0.8 dL/g generally lacks sufficient molecular weight to provide suitable mechanical properties for surgical devices, and an inherent viscosity above about 4.0 dL/g is generally too viscous for melt processing.

After the desired copolymer is prepared, filaments exhibiting the requisite properties for use as surgical sutures may be prepared using conventionally accepted methods well known in the art by first melt extruding the copolymer through a spinnerette to prepare fibers, drawing the fibers to create molecular orientation, and then annealing the oriented fibers to enhance their performance characteristics. See, for example, U.S. Pat. Nos. 4,643,191 and 4,653,497, and 5,007,923 which also describe in detail the testing procedures suitable for determining the mechanical and biological properties of the monofilaments described in the attached examples.

As the term is used in the claimed invention, the in vitro breaking strength retention (BSR) is a measure of the ability of a fiber to retain its strength after incubation in a buffer solution maintained at a constant temperature, usually 37° C. or 50° C. It is the ratio of the breaking strength of the fiber after a predetermined incubation period to the original breaking strength of the fiber before incubation. BSR is usually expressed as a percentage of the original breaking strength remaining after the predetermined incubation time. The procedures for determining the in vitro BSR have been well documented and are described in the U.S. Pat. No. 4,643,191.

Similarly, an in vivo BSR is a measure of the ability of a fiber to retain its initial strength after implantation in an animal, e.g. a rat. An in vivo BSR is the ratio of the breaking strength of an implanted fiber after a predetermined period of time to the breaking strength of the fiber before implantation. The procedures for determining the in vivo BSR have been well documented and are described in the patent cited above.

Another common suture property which is important to determine is the in vivo absorption profile. The in vivo absorption profile describes the amount of suture material still present at the surgical site in an animal, e.g., a rat, after a certain period of time. The amount of suture material is estimated by measuring the median percent of the original cross-sectional area of the suture remaining after intramuscular implantation for a specified period of time. The procedures for determining the in vivo absorption profile are described in numerous patents, for example, U.S. Pat. No. 4,653,497.

Although the in vitro or in vivo BSR and the in vivo rate of absorption can be modified significantly to tailor such properties for a specific operative procedure, it is desirable to make such changes without sacrificing mechanical properties. In preferred embodiments, the straight tensile strength of a monofilament prepared from the copolymers of this invention is greater than 25 kpsi, preferably greater than 50 kpsi, and the knot tensile strength is greater than 20 kpsi, preferably greater than 30 kpsi. Additionally, the Young's modulus of such an annealed monofilament is less than 1,300 kpsi, preferably less than 1,000 kpsi, and the percent elongation is less than 100 percent, preferably less than 75 percent.

In another embodiment of the present invention, the inventive copolymers may also be used as coatings for sutures and the like to improve the knot strengths and the tiedown properties, as well as to reduce the tissue drag of sutures. Conventional coating procedures can be used to apply the coating to sutures. A preferred method of applying the coating is to continuously pull the suture to be coated through a solution containing in the range of from about 1 to about 20 weight percent copolymer in a vertical direction to insure uniform drainage. The freshly coated fiber would then be pulled continuously through a drying tunnel, taken up on a wind-up wheel and vacuum dried overnight at room temperature.

This coating is ideally suited for applying to braided sutures, since braided sutures generally have chattery or rough tie-down properties. The coating may be applied to monofilament or braided absorbable or nonabsorbable sutures. Suitable absorbable sutures may be made from naturally absorbable materials including but not limited to catgut and collagen or synthetic absorbable materials including but not limited to homopolymers of glycolide, L-lactide, ε-caprolactone, and 1,4-dioxanone and copolymers of glycolide, L-lactide, D,L-lactide, ε-caprolactone, trimethylene carbonate, 1,4-dioxanone, 1,5-dioxepan-2-one and 1,4-dioxepan-2-one. Suitable nonabsorbable sutures may be made from naturally occurring, nonabsorbable materials including but not limited to silk, cotton, and linen or synthetic nonabsorbable materials including but not limited to polyesters, polyamides (i.e. nylon, nylon 6, nylon 66 etc.), and polyolefins (i.e. polyethylene and polypropylene).

The following examples are intended to illustrate the preferred embodiments and are in no way intended to limit the scope of the claimed invention. As used in Table II, PDP, PDO, PGA and PLA refer to polymers of 1,4-dioxepan-2-one, 1,4-dioxan-2-one, glycolide and L-lactide, respectively.

EXAMPLE 1

Synthesis of 1,5,8,12-Tetraoxacyclotetradecane-7,14-dione

In a glove box, 115 grams (5.00 moles) of sodium metal, in the form of freshly cut bars approximately 4 by 4 by 16 millimeters in size, were added to a five liter, three neck round bottom flask containing two liters of 1,3-propanediol. The reaction flask was transferred into an exhaust hood and fitted with a mechanical stirrer, a reflux condenser, and a dry nitrogen gas inlet and vent. The gas inlet was attached to one of the outer ground glass joints of the round bottom flask, and the vent was attached to the top of the reflux condenser and connected to a bubbler with tubing. The sodium metal was added in two equal portions with about eight hours in between additions. The reaction flask was immersed in a large oil bath. The temperature of the oil bath usually rose 10° C. to 15° C. during the exothermic reaction of sodium and 1,3-propanediol (caution: hydrogen gas is evolved). The sodium suspension was stirred vigorously under dry nitrogen gas for twenty four hours.

The small bars of sodium were cut from a large piece of sodium stored in a jar containing enough kerosene to cover the metal. The piece of sodium was blotted dry with a paper towel. It was then cut into small bars using the dull edge of a spatula, rinsed briefly in methanol, and stored in a tared beaker containing enough toluene to cover the sodium bars. After reweighing the beaker filled with sodium, the metal bars were transferred into the reaction flask with a pair of large tweezers.

After the sodium and the 1,3-propanediol had reacted for twenty four hours at room temperature, the sodium suspension was heated slowly to 150° C. The remaining sodium melted and reacted rapidly around 100° C. to form a transparent solution. The sodium suspension should not be heated before it has reacted at least twenty four hours without external heating, because the reaction will proceed to rapidly to control. When the oil bath reached 150° C., a one liter pressure equalizing addition funnel was attached. The nitrogen gas inlet was connected to the top of the dropping funnel. 236.5 grams (2.50 moles) of chloroacetic acid was melted and diluted immediately with 700 mL of 1,3-propanediol in a one liter Erlenmeyer flask. This hot chloroacetic acid solution was prepared in the hood, transferred into the addition funnel, and then added slowly over the next 30 minutes under dry nitrogen gas and with vigorous stirring. Usually, the oil bath temperature rose 5° C. to 10° C., and some sodium chloride crystallized out of solution during the addition. Vigorous stirring was continued for six hours, and then, the reaction mixture was allowed to cool down to room temperature, The addition funnel and reflux condenser were replaced by a still head and glass stopper. The excess 1,3-propanediol was removed by vacuum distillation. The oil bath temperature was kept between 130° C. and 160° C., while the still head temperature was approximately 110° C. When the distillation was over, the salt residue was allowed to cool down to 120° C. in the oil bath. Then, one liter of aqueous hydrochloric acid, prepared by mixing 500 mL of concentrated hydrochloric acid and 500 mL of distilled water, was added to the hot salt residue and stirred vigorously for 30 minutes. The reaction vessel was removed from the oil bath and allowed to cool to room temperature. The suspended sodium chloride crystals were removed by vacuum filtration, and the filtercake washed with one liter of ethanol. The ethanol caused more sodium chloride to crystallize out of solution. The filtrate was transferred into a four liter Erlenmeyer flask and diluted with three liters of ethanol. After standing overnight, the suspension was filtered again, and the aqueous ethanol was removed by distillation under dry nitrogen gas. Three more liters of ethanol were added and distilled off. The crude product, 6-hydroxy-3-oxa-caproic acid, was a dark brown liquid at this stage. Usually, 220 to 320 grams of material were isolated depending on the amount of residual water.

The crude hydroxyacid was vacuum filtered into a tared round bottom flask containing a magnetic stirring bar. Enough $(MgCO_3)_4.Mg(OH)_2.5H_2O$ was added to make a 0.5 to 1.0 weight percent solution. A distillation apparatus was attached having a 25 cm path length. The mixture was heated with a oil bath to 250° C. under nitrogen for about four hours to form low molecular weight polymers. Sometimes, more water distilled out at this point. The dark viscous liquid was allowed to cool. Then, the mixture was vacuum distilled, and a middle fraction was collected usually between 100° C. and 120° C., while the oil bath temperature was between 260° C. and 310° C. Frequently, forced air cooling was required instead of water, because the cyclic dimer of 1,4-dioxepan-2-one, namely 1, 5, 8, 12-tetraoxacyclotetradecane-7, 14-dione, (D), crystallized out in the condenser. A hot air gun was usually used to heat the middle section of the still head to maintain a reasonable distillation rate. The distilled product was sometimes a suspension of 1, 5, 8, 12-tetraoxacyclotetradecane-7, 14-dione crystals and a supernatant liquid. The collection flask was placed in the refrigerator overnight to enhance the crystallization of the 1, 5, 8, 12-tetraoxacyclotetradecane-7, 14-dione. These crystals were isolated by suction filtration, washed with cold ethyl acetate until they were completely white, and then recrystallized from boiling hot ethyl acetate (c=1 gram/6 mL). After standing overnight at room temperature, the recrystallized cyclic dimer of 1,4-dioxepan-2-one was collected by suction filtration, washed with cold ethyl acetate, and vacuum dried at 50° C. for twelve hours. Typical yields of recrystallized 1, 5, 8, 12-tetraoxacyclotetradecane-7, 14-dione were approximately five percent by weight of the original crude 6-hydroxy-3-oxa-caproic acid. MP 135°-136° C. at 2° C./minute (uncorrected) IR (KBr pellet, cm$^{-1}$) 2940, 1730, 1315, 1300, 1232, 1224, 1105, 1095, 1055, 1040, 950, 935, 760. $^1$H NMR (300 MHz, CDCl$_3$, ppm) $\delta$1.97 [quintet, 2H], 3.67 [triplet, 2H], 4.10 [singlet, 2H], 4.38 [triplet, 2H]. The 1, 5, 8, 12-tetraoxacyclotetradecane-7, 14-dione was determined to be greater than 99.5 mole percent pure by proton NMR spectroscopy. {$^1$H}$^{13}$C NMR (75 MHz, CDCl$_3$, ppm) $\delta$28.6, 60.9, 67.0, 69.2, 170.7.

The filtrate from the distilled product was recycled to prepare more 1, 5, 8, 12-tetraoxacyclotetradecane-7, 14-dione, that is, more magnesium carbonate was added and the mixture redistilled as described above. This filtrate was composed of 1,4-dioxepan-2-one, its cyclic dimer, and acyclic oligomers of 6-hydroxy-3-oxa-caproic acid. Two equivalents of methyl chloroacetate may be substituted for one equivalent of chloroacetic acid in this procedure. When methyl chloroacetate is employed, the crude product is methyl 6-hydroxy-3-oxa-caproate.

EXAMPLE 2

Polymerization of 1,5,8,12-Tetraoxacyclotetradecane7,14-dione

In a glove box, 43.3 grams (187 mmol) of recrystallized 1,5,8,12-tetraoxacyclotetradecane-7,14-dione, 14 μL (0.15 mmol) of vacuum distilled diethylene glycol (DEG), and 113 μL (37.7 μmol) of a 0.33 M stannous octoate solution in toluene were transferred into a clean, silanized, flame dried, 100 mL, two neck, round bottom flask. A flame dried vacuum adapter and a stirring assembly were fitted into the center ground glass joint. The stirring assembly consisted of a metal stirring rod and a teflon bearing. The side ground glass joint was stoppered with a glass stopper. A vacuum hose was attached to the vaccum port and clamped off with a hemostat. The reaction vessel was moved into an exhaust hood. The hose was connected to a nitrogen gas line via a Firestone valve. The flask was immersed in an oil bath set a 185° C. An inert atmosphere was maintained throughout the reaction. The melt viscosity increased steadily and eventually mechanical stirring was stopped. Aliquots were removed through the side joint under a strong nitrogen gas stream at two, four, six, and twenty four hours After one day at 185° C. the reaction vessel was removed from the oil bath and wrapped with aluminum foil. The polymer was allowed to stand and crystallize at room temperature for three days. The polymer was isolated by freezing the flask in liquid nitrogen. The flask broke away from the polymer. Some glass adhered to the polymer and was removed by grinding. The polymer was allowed to warm up to room temperature under a nitrogen atmosphere.

1,5,8,12-Tetraoxacyclotetradecane-7,14-dione polymerized to high conversion under these reaction conditions. Table I lists the percent conversion of this polymerization reaction as a function of time. The percent conversion was calculated using 300 MHz $^1$H NMR spectroscopy (CDCl$_3$) by integrating the areas under the methylene triplets located at $\delta$4.30 for poly[1,4-dioxepan-2-one](PDP) and at $\delta$4.38 for 1,5,8,12-tetraoxacyclotetradecane-7,14-dione.

TABLE I

| CONVERSION DATA FOR THE POLYMERIZATION OF 1,5,8,12-TETRAOXACYCLOTETRADECANE-7,14-DIONE ||
|---|---|
| TIME (hours) | PERCENT CONVERSION (mole %) |
| 2 | 88.7 |
| 4 | 94.4 |
| 6 | 96.8 |
| 24 | 98.3 |

The poly[1,4-dioxepan-2-one]exhibited an inherent viscosity of 2.0 dL/g in hexafluoroisopropanol (HFIP) at 25° C. (c=0.10 g/dL). The number average molecular weight was 31,000 daltons and the weight average molecular weight was 74,000 daltons as determined by gel permeation chromatography (GPC) using polymethacrylate (PMMA) standards. IR (thin film cast from a methylene chloride solution onto a KBr plate, cm$^{-1}$) 2970,1775, 1435, 1275, 1200, 1140, 1050. $^1$H NMR (300 MHz, CDCl$_3$, ppm) $\delta$1.96 [quintet, 2H], 3.64 [triplet, 2H], 4.08 [singlet, 2H], 4.30 [triplet, 2H]. The glass transition temperature of poly[1,4-dioxepan-2-one]was −36° C., and the melting point was 47° C. as measured by differential scanning calorimetry (DSC) at 20° C./minute under nitrogen.

The molar ratio of 1,5,8,12-tetraoxacyclotetradecane-7,14-dione to stannous octoate was 5000:1 in this example. The rate of polymerization can be increased by using a higher concentration of stannous octoate as the Lewis acid catalyst as described in Example 3, where the molar ratio of 1,5,8,12-tetraoxacyclotetradecane-7,14-dione to stannous octoate was 2000:1. The molecular weight was determined by the molar ratio of 1,5,8,12-tetraoxacyclotetradecane-7,14-dione to diethylene glycol or another suitable initiator.

EXAMPLE 3

Polymerization of 1,5,8,12-Tetraoxacyclotetradecane-7,14-dione

In a glove box, 40.0 grams (172 mmol) of recrystallized 1,5,8,12-tetraoxacyclotetradecane-7,14dione, 32 $\mu L$ (0.15 mmol) of vacuum distilled diethylene glycol, and 260 $\mu L$ (86.7 $\mu$mol) of a 0.33M stannous octoate solution in toluene were transferred into a clean, silanized, flame dried, 100 mL round bottom flask. A flame dried vacuum adapter and a stirring assembly were fitted into the ground glass joint. The stirring assembly consisted of a metal stirring rod and a teflon bearing. A vacuum hose was attached to the vaccum port and closed off with a clamp. The reaction vessel was moved into an exhaust hood. The hose was connected to a nitrogen gas line via a Firestone valve. The flask was immersed in an oil bath set a 185° C. for one hour. An inert atmosphere was maintained throughout the reaction. The 1,5,8,12-tetraoxacyclotetradecane-7,14-dione melted and polymerized rapidly. Mechanical stirring was stopped after only ten minutes because the melt viscosity was so high. The reaction vessel was removed from the oil bath and wrapped with aluminum foil. The polymer was allowed to stand and crystallize at room temperature for three days. The polymer was isolated by freezing the flask in liquid nitrogen. The flask broke away from the polymer. Some glass adhered to the polymer and was removed by grinding. The polymer was allowed to warm up to room temperature under a nitrogen atmosphere. 34.1 grams of poly[1,4-dioxepan-2-one]were collected (85 percent yield). The percent conversion was 97.9 mole percent as measured by proton NMR spectroscopy, and the inherent viscosity was 2.2 dL/g in HFIP at 25° C. (c=0.10 g/dL).

The polymer was dissolved in 340 mL of chloroform, suction filtered, and then transferred into a 500 mL separatory funnel. The solution was added dropwise into a large stainless steel blender containing 3.4 liters of methanol. The precipitated PDP was placed into a dish and vacuum dried at room temperature overnight. 29.4 grams were isolated (86% recovery). No 1,5,8,12-tetraoxacyclotetradecane-7,14-dione was detected by proton NMR spectroscopy in the precipitated polymer. The inherent viscosity of the PDP was 2.2 dL/g in HFIP at 25° C. (c=0.10 g/dL).

EXAMPLE 4 in vitro Hydrolysis of Poly[1,4-dioxepan-2-one]

111 Milligrams of poly[1,4-dioxepan-2-one]-(I.V.=1.15 dL/g; $M_n$=17,000; $M_w$=40,000; 1.5 mole % residual cyclic dimer) were placed in a beaker and suspended in 100 mL of phosphate buffer (PBS) pH 7.27. The beaker was placed in a water bath set at 50° C. The poly[1,4-dioxepan-2-one]took twenty four days to melt, swell, hydrolyze, and dissolve into soluble molecular species. This hydrolysis experiment was carried out at a temperature above the melting range of poly[1,4-dioxepan-2-one], and consequently, showed that rubbery, amorphous poly[1,4-dioxepan-2-one]was hydrolyzed in phosphate buffer. Poly[1,4-dioxepan-2-one] would be expected to hydrolyze more slowly at temperatures below its melting point, for example, under physiological conditions.

EXAMPLE 5 in vivo Tissue Reaction and Absorption 2.3 Grams of poly[1,4-dioxepan-2-one]made in Example 3 were dissolved in 9.1 grams of tetrahydrofuran in a 25 mL Erlenmeyer flask. The resulting viscous solution was suction filtered. More tetrahydrofuran was added to the filtrate to obtain a twenty weight percent solution (some tetrahydrofuran was removed by the vacuum filtration operation). In a vented glove box, the filtered solution was poured into a clean, silanized dish having a diameter of 8.5 centimeters. The dish was covered with a large beaker to slow the rate of evaporation. A clear film had formed after about five hours. The film was stored at room temperature under a nitrogen atmosphere for about twenty five days. The film was now translucent, cut into two large pieces with a razor blade, and then vacuum dried at room temperature for 163 hours. The two pieces of film were cut into 30 rectangular strips about 5 millimeters wide and 20 millimeters long. These strips of poly[1,4-dioxepan-2-one]were placed in packages, sterilized by exposure to ethylene oxide, and sealed under an inert atmosphere.

The sterilized strips of poly[1,4-dioxepan-2-one] were implanted in rats intramuscularly, and the tissue reaction and absorption rate were observed. The early tissue reaction at three and seven days was slight to moderate. Nothing unusual was observed. At 119 days, there was still a significant amount of poly[1,4-dioxepan2-one]present. After 224 days, however, the entire implant of poly[1,4-dioxepan-2-one]had absorbed completely.

EXAMPLE 6

Synthesis and Polymerization of 1,4-Dioxepan-2-one 271.2 Grams (2.02 moles) of crude 6-hydroxy-3-oxacaproic acid, as prepared in Example 1, 3.5 liters (87 moles) of reagent grade methanol, and 0.2 grams (2 mmol) of concentrated sulfuric acid were charged into a five liter, round bottom flask containing some boiling chips. A reflux condenser connected to a dry stream of nitrogen gas via tubing was attached, and the solution was heated to reflux with an oil bath for twenty four hours. After the solution had cooled down, 5.00 grams (59.5 mmol) of sodium bicarbonate were added, and a distillation head was attached. The methanol was distilled off at atmospheric pressure. After the methanol was removed, the orangish brown residue was vacuum filtered into a tared, one liter round bottom flask containing a magnetic stirring bar. 297 grams of crude methyl 6-hydroxy-3-oxa-caproate were collected (99.0% yield). A still head was attached, and the crude product was vacuum distilled. Initially, a colorless liquid distilled over between 88° C. and 90° C. (0.01 mm Hg), but the distillation rate eventually slowed down. After two hours, some crystals of 1,5,8,12-tetraoxacyclotetradecane-7,14-dione formed in the condenser. The distillation was stopped. The collection flask was placed in the refrigerator overnight. Crystals of 1,5,8,12-tetraoxacyclotetradecane-7,14-dione formed in the collection flask and were removed by suction filtration. These crystals were washed with 100 mL of ethyl acetate and air dried. 4.11 grams of 1,5,8,12-tetraoxacyclotetradecane-7,14-dione and 67.5 grams of supernatent liquid A were isolated.

0.50 Grams of $(MgCO_3)_4 \cdot Mg(OH)_2 \cdot 5H_2O$ (1 mmol) were added to the residue left in the distillation pot. The vacuum distillation was continued at a much higher pot temperature ranging from 260° C. to 310° C. Initially, an almost colorless liquid distilled out, and the rate of distillation was much greater than without catalyst. The distillate slowly turned yellow with time. Some 1,5,8,12-tetraoxacyclotetradecane-7,14-dione also crystallized out of the distillate. 6.30 grams of 1,5,8,12-tetraoxacyclotetradecane-7,14-dione and 80.0 grams of supernatent liquid B were isolated as described previously. The weak O-H band in the infrared spectrum of supernatent liquid B was encouraging at this point and suggested the presence of some 1,4-dioxepan-2-one. Moreover, the fingerprint region of its infrared spectrum was relatively sharp and indicated that supernatent liquid B was fairly pure.

76.5 grams of supernatent liquid B were transferred into a 100 mL pear shaped flask containing a magnetic stirring bar. The sample was bright yellow. A still head was attached and the material was vacuum distilled. The oil bath temperature was between 150° C. and 155° C., the distillate temperature was dependent on the reflux ratio as the sample did not distill smoothly. 40.5 grams of yellow liquid C were collected in the middle fraction (53% recovery). The infrared spectrum of this crude 1,4-dioxepan-2-one had a more defined fingerprint region than the starting material B. However, the weak hydroxyl band around 3500 cm$^{-1}$ was indicative of hydroxyl impurities. The residue left in the reaction vessel had a relatively strong hydroxyl band as well as broad bands in the fingerprint region characteristic of a mixture of oligomers.

The crude monomer was then distilled from liquid MDI (Isonate 143L) in an attempt to remove the hydroxyl impurities. 2.85 grams of Isonate 143L were added to liquid C. A magnetic stirring bar was added, and the mixture was vacuum distilled. A forerun and a middle fraction were collected at a still head temperature range between 68° C. and 72° C. (0.01 mm Hg) while the oil bath temperature was maintained between 110° C. and 115° C. 26.8 grams of a colorless liquid, labelled D, were collected as the middle fraction. The infrared spectrum of sample D showed a very weak hydroxyl band and a very sharp fingerprint region that indicated the presence of 1,4-dioxepan-2-one of high purity. IR (thin film on KBr plates, cm$^{-1}$): 3500 (weak), 2970, 2820, 1735, 1300, 1230, 1210, 1115, 1075, and 1020. $^1$H NMR (300 MHz, HFAD/C$_6$D$_6$, ppm): $\delta$1.55 pentet (2H), 3.45 triplet (2H), 3.90 triplet (2H), and 3.95 (2H). The middle fraction was determined to be greater than 99 mole percent pure by proton NMR spectroscopy. This is a very different $^{-1}$H NMR spectrum than the corresponding cyclic dimer, 1,5,8,12-tetraoxacyclotetradecane-7,14-dione, which had the following $^1$H NMR spectrum (300 MHz, HFAD/C$_6$D$_6$, ppm): $\delta$1.70 pentet (2H), 3.35 triplet (2H), 3.90 singlet (2H), and 4.15 triplet (2H). The index of refraction at 22° C. of 1,4-dioxepan-2-one (sample D) was 1.4592 which was similar to that of $\epsilon$-caprolactone as expected. The index of refraction of distilled $\epsilon$-caprolactone was 1.4623 at 22° C. Mass spectroscopy (DIP) confirmed the molecular weight of sample D. A molecular ion $[M+H]^+$ of 117 was detected. However, ions of larger mass to charge ratio were also detected which is consistent with the presence of small amounts of cyclic dimer or oligomer in this sample of 1,4-dioxepan-2-one.

In order to get some idea about the polymerizability and purity of sample D, its forerun was polymerized on the same day that it was prepared. 5.00 grams (43.1 mmol) of the forerun 1,4-dioxepan-2-one, 3.0 $\mu$L (32 $\mu$mol) of distilled DEG, and 10 $\mu$L (3.3 $\mu$mol) of a 0.33M solution of stannous octoate were transferred into a clean, flame dried ampoule containing a magnetic stirring bar. The ampoule was stoppered with a rubber septum which was wired down. The molar ratio of 1,4-dioxepan-2-one to DEG was 1,300:1 and the molar ratio of 1,4-dioxepan-2-one to stannous octoate was 13,000:1.

The ampoule was immersed in an oil bath set at 185° C. for 16 hours. After forty minutes, the mixture was dark amber in color and was slightly viscous. The polymer was allowed to crystallize over several days time. The tan solid was isolated by freezing the ampoule in liquid nitrogen whereupon the glass ampoule broke apart. The poly[1,4-dioxepan-2-one] had an inherent viscosity of 0.48 dL/g in HFIP at 25° C. (c=0.10 g/dL) and contained 2.7 mole percent residual monomer as determined by $^1$NMR spectroscopy. Consequently, it appeared that sample D was not pure enough to yield high molecular weight poly[1,4-dioxepan-2-one], at least, under these reaction conditions.

A portion of liquid D was also polymerized by adding only the stannous octoate as the Lewis acid catalyst relying on the hydroxyl impurities to act as the initiators of the polymerization. The molar ratio of 1,4-dioxepan-2-one to stannous octoate was 15,000:1; the polymerization proceeded to 98.2 percent conversion in 24 hours at 185° C.; and an inherent viscosity of only 0.45 dL/g was obtained. When the molar ratio of monomer to stannous octoate was reduced to 25,000:1 under the same reaction conditions, the polymerization proceeded to 98.4 percent conversion, and an inherent viscosity of 0.81 dL/g was obtained. Based on these data, the polymerizability of 1,4-dioxepan-2-one was found to be sensitive to the level of Lewis acid catalyst at temperatures commonly used to successfully polymerize $\epsilon$-caprolactone. Thermal or photodegradation may also be a problem. It was decided to react liquid D with some trimethylchlorosilane in an attempt to convert the hydroxyl impurities into more volatile molecules that could be removed during a subsequent vacuum distillation.

0.74 Grams (7.2 mmol) of trimethylchlorosilane were added to the remainder of sample D. The solution stood at room temperature for 48 hours and turned orangish brown. 21.0 grams of this mixture were transferred into a 50 mL pear shaped flask containing a magnetic stirring bar. A distillation head and fraction cutter were attached. The sample was degassed overnight by applying a high vacuum. The reaction vessel was heated with an oil bath. When the oil bath had reached a temperature of 115° C., the monomer started to distill out. A slightly discolored forerun was collected, and then, a colorless middle fraction was collected between 87° C. and 89° C. (0.01 mm Hg) and labelled sample E. The pot temperature increased slowly during the distillation to 125° C., and the pot did not decompose as in many previous runs. The infrared spectrum of the forerun showed a very weak hydroxyl band, while the middle fraction E showed no hydroxyl band at all. Both samples had very sharp fingerprint regions. IR (thin film on KBr, cm$^{-1}$): 2970, 2920, 2870, 1735, 1295, 1230, 1210, 1110, 1075, 1020, and 830. Sample E was determined to be greater than 98.3 mole percent pure by proton NMR spectroscopy. 1,5,8,12-Tetraoxacyclotetradecane-7,14-dione appeared to be the only impurity present.

The polymerizability of 1,4-dioxepan-2-one, sample E, was tested. 2.00 grams (17.2 mmol) of sample E, 1.0 µL (11 µmol) of distilled DEG, and 2.0 µL (69 µmol) of a 0.33M stannous octoate solution in toluene were transferred into a clean, flame dried, silanized ampoule containing a magnetic stirring bar. The ampoule was stoppered with a rubber septum which was wired down. The molar ratio of 1,4-dioxepan-2-one to DEG was 1,500:1 and the molar ratio of 1,4-dioxepan-2-one to stannous octoate was 25,000:1. The ampoule was placed in an oil bath set at 185° C. for 24 hours. The melt viscosity increased slowly, but after two hours, the melt viscosity was too high for further magnetic stirring. The polymer melt was light yellow at this point. After 24 hours, the melt was yellow and viscous. The melt viscosity apparently decreased during the night probably due to some degradation reactions. The polymer melt was allowed to crystallize before the ampoule was broken in liquid nitrogen. The poly[1,4-dioxepan-2-one]had an inherent viscosity of 0.63 dL/g in HFIP at 25° C. (c=0.10 g/dL). Sample E polymerized to 99.2 percent conversion as determined by proton NMR spectroscopy. There were 0.3 mole percent residual 1,4-dioxepan-2-one and 0.4 mole percent residual 1,5,8,12-tetraoxacyclotetradecane-7,14-dione present in the polymer. So, in short, 1,4-dioxepan-2-one polymerized to high conversion at 185° C. but only to moderate molecular weight, suggesting that the temperature may have been too high to obtain high molecular weight polymers. Consequently, we have used the cyclic dimer of 1,4-dioxepan-2-one, 1,5,8,12-tetraoxacyclotetradecane-7,14-dione, to prepare high molecular weight poly[1,4-dioxepan-2-one] instead of the simple seven member ring lactone. 1,5,8,12-Tetraoxacyclotetradecane-7,14-dione, as already described in Examples 1–3, is a thermally stable, crystalline solid which is easily purified by recrystallization from ethyl acetate and polymerizes to high conversion and high molecular weight at 185° C.

EXAMPLE 7

Preparation of a Segmented Block Copolymer from Glycolide and Poly[1,4-dioxepan-2-one]

In a glove box, 5.00 grams (43.1 mmoles of repeating units) of precipitated poly[1,4-dioxepan-2-one]-(I.V.=1.33 dL/g), 10.0 grams (86.2 mmoles) of glycolide (G), and 5.2 µL (1.7 µmoles) of a 0.33M stannous octanoate solution in toluene were added into a flame dried, 100 mL round bottom flask equipped with a flame dried mechanical stirrer and vacuum port. The flask was attached to a vacuum manifold for two hours to dry using a section of vacuum hose and then transferred into a hood under an inert atmosphere. The flask was connected to a nitrogen line and immersed in an oil bath set at 100° C. An inert atmosphere was maintained inside the reaction vessel throughout the polymerization. The glycolide melted and the poly[1,4-dioxepan-2-one]softened. The temperature was increased slowly over the next thirty minutes to 200° C. and held there for two hours. The poly[1,4-dioxepan-2-one]dissolved in the molten glycolide to form a homogeneous solution without any mixing problems. By the time the temperature was 200° C., the melt viscosity was so high that mechanical stirring was stopped. After forty minutes, the poly[glycolic acid](PGA) blocks started to crystallize out of the copolymer melt. The block copolymer was isolated by breaking the flask in liquid nitrogen. 9.50 grams of copolymer were isolated. The inherent viscosity was 1.4 dL/g in HFIP at 25° C. (c=0.10 g/dL). The number average molecular weight was 30,000 daltons, and the weight average molecular weight was 58,000 daltons as measured by GPC in HFIP using PMMA standards. The block copolymer was devolatized at 80° C. for 72 hours and lost 0.14 grams of weight (1.5% weight loss). The chemical composition of the segmented copolymer was determined by 300 MHz proton NMR spectroscopy to consist of 81.7 mole percent of PGA repeating units and 18.3 mole percent of PDP repeating units. The melting point was observed between 220° C. and 224° C. by hot stage optical microscopy.

The segmented block copolymer was spun and drawn into a fiber. The fiber was stretched on a rack and annealed at 110° C. for 6 hours. The annealed fiber (diameter 9.7 mils) had a straight tensile strength of 65 kpsi, a knot tensile strength of 41 kpsi, a Young's modulus of 300 kpsi, and an elongation to break of 30 percent. This fiber was then implanted intramuscularly in rats and its in vivo breaking strength retention (BSR) profile measured. The fiber retained 62 percent of its original straight tensile strength after seven days of implantation; 18 percent after fourteen days; and no measured strength after twenty one days.

EXAMPLE 8

Preparation of a Segmented Block Copolymers from Glycolide and Poly[1,4-dioxepan-2-one]

In a glove box, 5.00 grams (43.1 mmoles of repeat units) of precipitated poly[1,4-dioxepan-2-one]-(I.V.=1.5 dL/g; $M_n$=34,000; $M_w$=54,000), 22.5 grams (194 mmoles) of glycolide, and 12 µL (3.9 µmoles) of a 0.33M stannous octanoate solution in toluene were added into a flame dried, 100 mL round bottom flask equipped with a flame dried mechanical stirrer and vacuum port. The flask was attached to a vacuum manifold overnight to remove the toluene and other volatile compounds using a section of vacuum hose. Then, the reaction flask was transferred into a hood under an inert atmosphere. The flask was connected to a nitrogen gas line and immersed in an oil bath set at 100° C. An inert atmosphere was maintained inside the reaction vessel throughout the polymerization. The glycolide melted and the poly[1,4-dioxepan-2-one]softened. The temperature was increased slowly over the next thirty minutes to 185° C. and held there for two hours. The poly[1,4-dioxepan-2-one]dissolved in the molten glycolide to form a homogeneous solution. Shortly after reaching 185° C., mechanical stirring was discontinued because the melt viscosity was high enough to exhibit rod climbing. After fifty minutes, the PGA blocks started to crystallize out of the copolymer melt. The copolymer became opaque and tan in color. The segmented block copolymer was isolated by breaking the flask in liquid nitrogen, deglassed by grinding, ground in a Wiley mill, and then sifted through a sieve. 20.1 grams of copolymer were isolated. The inherent viscosity was 2.6 dL/g in HFIP at 25° C. (c=0.10 g/dL). The block copolymer was vacuum dried at 80° C. for 24 hours, but no weight loss occurred. The inherent viscosity was still 2.6 dL/g in HFIP at 25° C. (c=0.10 g/dL) after devolatization.

copolymerizations as well as the one described above are listed in Tables II, III, and IV.

TABLE II

CHARACTERIZATION DATA FOR SEGMENTED BLOCK COPOLYMERS OF PGA AND PDP

| SAMPLE[1] | COPOLYMER COMPOSITION (mole %) | | | | MOLECULAR WEIGHT (daltons) | | | THERMAL PROPERTIES (°C.) | |
|---|---|---|---|---|---|---|---|---|---|
| | PGA | PDP[2] | G | D | IV (dl/g) | $M_n$ | $M_w$ | $T_g$ | $T_m$ |
| 8-F | 99.7 | 0 | 0.3 | 0 | — | — | — | — | — |
| 8-G | 91.4 | 4.8 | 3.7 | 0.1 | — | 31,000 | 62,000 | 43 | 223 |
| 8-H | 90.4 | 8.1 | 1.5 | 0.1 | 2.8 | 34,000 | 84,000 | 43 | 222 |
| 8-I | 89.3 | 8.9 | 1.7 | 0.1 | 2.6 | 46,000 | 101,000 | 43 | 223 |
| 8-J | 85.4 | 13.1 | 1.4 | 0.1 | 2.3 | 35,000 | 78,000 | 40 | 221 |

[1]Sample A was the homopolymer control, namely poly[gycolide].
[2]Samples B and C were prepared from a batch of PDP exhibiting an inherent viscosity of 2.2 dL/g; a number average molecular weight of 46,000; and a weight average molecular weight of 74,000. Samples D and E were prepared from a batch of PDP exhibiting an inherent viscosity of 15 dL/g; a number average molecular weight of 34,000; and a weight average molecular weight of 54,000.

TABLE III

FIBER PROPERTIES FOR SEGMENTED BLOCK COPOLYMERS OF PGA AND PDP

| | FIBER PROPERTIES | | | | |
|---|---|---|---|---|---|
| SAMPLE | DIAMETER (MILS) | STRAIGHT TENSILE STRENGTH (KPSI) | KNOT TENSILE STRENGTH (KPSI) | PERCENT ELONGATION | YOUNG'S MODULUS (KPSI) |
| 8-F* | 6.9 | 132 | 87 | 48 | 1900 |
| 8-G | 8.2 | 76 | 55 | 29 | 1200 |
| 8-H | 8.3 | 74 | 56 | 22 | 1300 |
| 8-I | 8.8 | 76 | 56 | 40 | 1000 |
| 8-J | 7.7 | 83 | 65 | 31 | 1100 |

*The tensile properties of PGA can be improved by changing the drawing and annealing conditions. Other PGA fibers exhibited straight tensile strengths between 170 and 210 kpsi, knot tensile strengths between 105-110 kpsi, and Young's moduli between 1900 and 2200 kpsi. Sample A in this table was drawn and annealed under the same conditions as used for the segmented block copolymers.

The number average molecular weight was 46,000 daltons, and the weight average molecular weight was 101,000 daltons as measured by GPC in HFIP using PMMA standards. The chemical composition of the segmented copolymer was determined by 300 MHz proton NMR spectroscopy to consist of 89.3 mole percent of PGA repeating units, 8.9 mole percent of PDP repeating units, 1.7 mole percent unreacted glycolide, and 0.1 mole percent of 1,5,8,12- tetraoxacyclotetradec-ane-7,14-dione. The glass transition temperature was 43° C. and the melting point was 223° C. as measured by DSC at a heating rate of 20° C. per minute under a nitrogen atmosphere. This sample was designated 8-I.

The segmented block copolymer was spun and drawn into a fiber. The fiber was stretched on a rack and annealed at 110° C. for 6 hours. The annealed fiber (diameter 8.8 mils) had a straight tensile strength of 76 kpsi, a knot tensile strength of 56 kpsi, a Young's modulus of 1000 kpsi, and an elongation to break of 40 percent. The in vitro BSR profile of the fiber made from I was measured in phosphate buffer pH 7.3 at 37° C. and at 50° C. At 37° C., the fiber 8-I retained 99 percent of its original straight tensile strength after four and seven days, while a PGA control fiber (8-F) only retained 87 percent of its tensile strength after four days and 47 percent after seven days At 50° C. the fiber 8-I retained 38 percent of its original straight tensile strength after four days, while a PGA control fiber 8-F only retained 11 percent of its tensile strength after four days. Both fibers lost all of their tensile strength after seven days in phosphate buffer at 50° C.

Similar experimental results were obtained for other segmented block copolymers of PGA and PDP of various chemical compositions. The results of these other

TABLE IV

In vitro BREAKING STRENGTH RETENTION DATA FOR SEGMENTED BLOCK COPOLYMERS OF PGA AND PDP

| | in vitro BREAKING STRENGTH RETENTION | | | |
|---|---|---|---|---|
| | 37° C./PBS/pH 7.3 | | 50° C./PBS/pH 7.3 | |
| SAMPLE | 4 DAYS | 7 DAYS | 4 DAYS | 7 DAYS |
| 8-F | 87 | 47 | 11 | 0 |
| 8-G | 97 | 94 | 22 | 0 |
| 8-H | 94 | 91 | 45 | 0 |
| 8-I | 99 | 99 | 38 | 0 |
| 8-J | 99 | 97 | 38 | 0 |

The data shown in these tables clearly demonstrate that segmented block copolymers consisting predominantly of PGA repeating units with a minor amount of PDP repeating units can be spun into useful fibers that are strong enough to be used as an absorbable suture material. These fibers exhibited Young's moduli about 40 percent lower on average than a typical PGA fiber depending on the exact chemical composition, even though the segmented block copolymers were greater than 85 mole percent PGA. These lower moduli should provide better handling properties to the suture. Furthermore, fibers of these segmented block copolymers of PGA and PDP exhibited longer BSR profiles than fibers of PGA homopolymer. The longer BSR profiles of these segmented block copolymers of PGA and PDP may better match the strength retention profile of a desired surgical device than pure PGA, while retaining sufficient tensile strength and elongation to break to function adequately.

EXAMPLE 9

Preparation of a Segmented Block Copolymers from L-Lactide and Poly[1,4-dioxepan-2-one]

In a glove box, 5.00 grams (43.1 mmoles of repeating units) of precipitated poly[1,4-dioxepan-2-one]- (I.V.=1.5 dL/g; $M_n$=34,000; $M_w$=54,000), 27.9 grams (194 mmoles) of L-lactide (L), and 23 μL (7.8 μmoles) of a 0.33M stannous octanoate solution in toluene were added into a flame dried, 100 mL round bottom flask equipped with a flame dried mechanical stirrer and vacuum port. The flask was attached to a vacuum manifold overnight to remove the toluene and other volatile compounds using a section of vacuum hose. Then, the reaction flask was transferred into a hood under an inert atmosphere. The flask was connected to a nitrogen gas line and immersed in an oil bath set at 120° C. An inert atmosphere was maintained inside the reaction vessel throughout the polymerization. The L-lactide melted and the poly[1,4-dioxepan-2-one]softened and dissolved in about 30 to 40 minutes at 120° C. The temperature was increased slowly over the next 10 minutes to 185° C. and held there for five hours. Fifteen minutes after reaching 185° C., mechanical stirring was discontinued because the melt viscosity was high enough to exhibit rod climbing. The segmented block copolymer was isolated by breaking the flask in liquid nitrogen, deglassed by grinding, ground in a Wiley mill, and then sifted through a sieve. 28.0 grams of copolymer were isolated. The segmented block copolymer was vacuum dried at 80° C. for 24 hours and lost 1.0 gram of volatile material. The inherent viscosity was 2.6 dL/g in HFIP at 25° C. (c=0.10 g/dL) after devolatization. The number average molecular weight was 58,000 daltons, and the weight average molecular weight was 112,000 daltons as measured by GPC in HFIP using PMMA standards. The chemical composition of the segmented copolymer was determined by 300 MHz proton NMR spectroscopy to consist of 72.4 mole percent of poly[L-lactide](PLA) repeating units, 25.5 mole percent of PDP repeating units, 2.0 mole percent of unreacted L-lactide, and 0.1 mole percent of 1,5,8,12-tetraoxacyclotetradecane-7,14-dione. The glass transition temperature was 44° C. and the melting point was 171° C. as measured by DSC at a heating rate of 20° C. per minute under a nitrogen atmosphere. Sample 9-Q.

The segmented block copolymer was spun and drawn into a fiber. The fiber was stretched on a rack and annealed at 110° C. for 6 hours. The annealed fiber (diameter 7.6 mils) had a straight tensile strength of 42 kpsi, a knot tensile strength of 43 kpsi, a Young's modulus of 560 kpsi, and an elongation to break of 62 percent. The in vitro BSR profile of the fiber 9-Q was measured in phosphate buffer pH 7.3 at 37° C. and at 50° C. At 37° C., the fiber 9-Q retained 96 percent of its original straight tensile strength after four days and 95 percent after seven days, while a PLA control fiber 9-K retained 100 percent of its tensile strength after both four and seven days. At 50° C., the fiber 9-Q retained 84 percent of its original straight tensile strength after four days and 75 percent after seven days, while a PLA control fiber 9-K retained 100 percent of its tensile strength after both four and seven days.

Similar experimental results were obtained for other segmented block copolymers of PLA and PDP of various chemical compositions. The results of these other copolymerizations as well as the one described above are listed in Tables V, VI, and VII.

TABLE V

CHARACTERIZATION DATA[1] FOR SEGMENTED BLOCK COPOLYMERS OF PLA AND PDP

| SAMPLE[2] | COPOLYMER COMPOSITION (mole %) | | | | MOLECULAR WEIGHT (DALTONS) | | | THERMAL PROPERTIES (°C.) | |
|---|---|---|---|---|---|---|---|---|---|
| | PLA | PDP[3] | L | D | IV (dL/g) | $M_n$ | $M_w$ | $T_g$ | $T_m$ |
| 9-K | 96.3 | 0 | 3.7 | 0 | 2.3 | 60,000 | 107,000 | — | — |
| 9-L | 89.3 | 5.0 | 5.6 | 0.1 | 2.7 | 69,000 | 139,000 | 47 | 176 |
| 9-M | 88.1 | 9.9 | 2.0 | 0.1 | 3.1 | 66,000 | 139,000 | 50 | 177 |
| 9-N | 86.5 | 11.7 | 1.5 | 0.1 | 1.9 | 55,000 | 121,000 | 46 | 173 |
| 9-O | 92.6 | 16.9 | 0.1 | 0.5 | 1.9 | 62,000 | 113,000 | — | — |
| 9-P | 76.7 | 22.4 | 0.6 | 0.1 | 1.5 | 33,000 | 60,000 | — | — |
| 9-Q | 72.4 | 25.5 | 2.0 | 0.1 | 2.6 | 58,000 | 112,000 | 44 | 171 |

[1]The polymer compositions were determined by 300 MHz $^1$H NMR spectroscopy. The inherent viscosities were measured in HFIP at 25° C. [c = 0.10 dL/g]. The number average and weight average molecular weights were measured by GPC in HFIP using PMMA standards. The glass transition temperatures and melting points were measured by DSC at 20° C./min under dry nitrogen gas.
[2]Sample A is the homopolymer control, namely poly[L-lacide].
[3]Samples B, C, and D were prepared from a batch of PDP exhibiting an inherent viscosity of 2.2 dL/g; a number average molecular weight of 46,000; and a weight average molecular weight of 74,000. Sample E was prepared from a batch of PDP exhibiting an inherent viscosity of 1.8 dL/g; a number average molecular weight of 44,000; and a weight average molecular weight of 69,000. Samples F and G were prepared from a batch of PDP exhibiting an inherent viscosity of 1.5 dL/g; a number av erage molecular weight of 34,000; and a weight average molecular weight of 54,000.

TABLE VI

FIBER PROPERTIES FOR SEGMENTED BLOCK COPOLYMERS OF PLA AND PDP

| | FIBER PROPERTIES | | | | |
|---|---|---|---|---|---|
| SAMPLE | DIAMETER (MILS) | STRAIGHT TENSILE STRENGTH (KPSI) | KNOT TENSILE STRENGTH (KPSI) | PERCENT ELONGATION | YOUNG'S MODULUS (KPSI) |
| 9-K | 7.4 | 61 | 45 | 87 | 1100 |
| 9-L | 7.5 | 52 | 43 | 61 | 790 |
| 9-M | 7.7 | 42 | 39 | 62 | 720 |
| 9-N | 8.0 | 36 | 27 | 61 | 490 |
| 9-O | 7.1 | 45 | 34 | 72 | 610 |

TABLE VI-continued
FIBER PROPERTIES FOR SEGMENTED BLOCK COPOLYMERS OF PLA AND PDP

| | FIBER PROPERTIES | | | | |
|---|---|---|---|---|---|
| SAMPLE | DIAMETER (MILS) | STRAIGHT TENSILE STRENGTH (KPSI) | KNOT TENSILE STRENGTH (KPSI) | PERCENT ELONGATION | YOUNG'S MODULUS (KPSI) |
| 9-P | 6.0 | 53 | 40 | 50 | 639 |
| 9-Q | 7.6 | 42 | 43 | 62 | 560 |

TABLE VII
In vitro BREAKING STRENGTH RETENTION DATA FOR SEGMENTED BLOCK COPOLYMERS OF PLA AND PDP

| | in vitro BREAKING STRENGTH RETENTION (%) | | | |
|---|---|---|---|---|
| | 37° C./PBS/pH 7.3 | | 50° C./PBS/pH 7.3 | |
| SAMPLE | 4 DAYS | 7 DAYS | 4 DAYS | 7 DAYS |
| 9-K | 100 | 100 | 100 | 100 |
| 9-L | 96 | 91 | 88 | 75 |
| 9-M | 95 | 99 | 89 | 89 |
| 9-N | 92 | 82 | 53 | 51 |
| 9-O | 89 | 79 | 81 | 63 |
| 9-P | 89 | 81 | 78 | 63 |
| 9-Q | 96 | 95 | 84 | 75 |

The data shown in these tables clearly demonstrate that segmented block copolymers consisting predominantly of PLA repeating units with a minor amount of PDP repeating units can be spun into useful fibers that are strong enough to be used as an absorbable suture material. These fibers exhibited Young's moduli about 42 percent lower on average than a typical PLA fiber depending on the exact chemical composition, even though the segmented block copolymers were greater than 75 mole percent PLA. These lower moduli should provide better handling properties to the suture. Furthermore, fibers of these segmented block copolymers of PLA and PDP exhibited shorter BSR profiles than fibers of the PLA homopolymer. The shorter BSR profiles were most clearly evident at 50° C. The shorter BSR profiles of these segmented block copolymers of PLA and PDP may better match the strength retention profile of a desired surgical device than pure PLA, while retaining sufficient tensile strength and elongation to break to function adequately.

EXAMPLE 10

Preparation of Statistically Random Copolymers of L-Lactide and 1,5,8,12-Tetraoxacyclotetradecane-7,14-dione In a glove box, 5.00 grams (21.6 mmoles) of 1,5,8,12-tetraoxacyclotetradecane-7,14-dione, 27.9 grams. (194 mmoles) L-lactide, 17 μL (0.18 mmoles) of distilled DEG, and 26 μL (8.6 μmoles) of a 0.33M stannous octanoate solution in toluene were added into a flame dried, 100 mL round bottom flask equipped with a flame dried mechanical stirrer and vacuum port. The flask was attached to a vacuum manifold overnight to remove the toluene and other volatile compounds using a section of vacuum hose. Then, the reaction flask was transferred into a hood under an inert atmosphere. The flask was connected to a nitrogen gas line and immersed in an oil bath set at 185° C. for 24 hours and then at 110° C. for 72 hours. After fifteen minutes at 185° C., mechanical stirring was discontinued because the melt viscosity had increased significantly and rod climbing was observed. An inert atmosphere was maintained inside the reaction vessel throughout the polymerization. The copolymer was grainy. We suspected that a bad batch of catalyst was used as other polymerization reactions using the same catalyst solution proceeded to low conversion and molecular weight. The statistically random copolymer was isolated by freezing the flask in liquid nitrogen where the glass broke away. The copolymer was vacuum dried at room temperature for 24 hours. Since the copolymer was still grainly, we decided to purify it by precipitation. 20.1 grams of the copolymer were dissolved in 200 mL of boiling hot chloroform. The hot solution was suction filtered and transferred into a separatory funnel. The solution was added dropwise into two liters of methanol with vigorous magnetic stirring in a four liter beaker. A stringy white copolymer precipitated out. Occasionally, large pieces of copolymer were removed from the suspension with a pair of tweezers to avoid stirring problems. The precipitated copolymer was isolated by vacuum filtration and rinsed with 500 mL of methanol. After being air dried on the Buchner funnel, the copolymer was vacuum dried at 50° C. for 40 hours. 16.9 grams of a stringy, white, powdery copolymer were isolated (84% recovery). The inherent viscosity was 1.3 dL/g in HFIP at 25° C. (c=0.10 g/dL) after precipitation. The number average molecular weight was 42,000 daltons, and the weight average molecular weight was 71,000 daltons as measured by GPC in HFIP using PMMA standards. The chemical composition of the statistically random copolymer was determmined by 300 MHz proton NMR spectroscopy and was found to consist of 95.1 mole percent of PLA repeating units, 4.5 mole percent of PDP repeating units, and not more than 0.4 mole percent residual 1,5,8,12-tetraoxacyclotetradecane-7,14-dione. The glass transition temperature was 64° C. and the melting point was 164° C. as measured by DSC at a heating rate of 20° C. per minute under a nitrogen atmosphere.

The precipitated copolymer was spun and drawn into a fiber. The fiber was stretched on a rack and annealed at 110° C. for 6 hours. The annealed fiber (diameter 7.8 mils) had a straight tensile strength of 46 kpsi, a knot tensile strength of 35 kpsi, a Young's modulus of 700 kpsi, and an elongation to break of 57 percent. The in vitro BSR profile of this annealed fiber was measured in phosphate buffer pH 7.3 at 50° C. The annealed fiber retained 88 percent of its original straight tensile strength after four days and 82 percent after seven days, while a PLA control fiber retained 100 percent of its tensile strength after both four and seven days.

EXAMPLE 11

Preparation of Statistically Random Copolymers of L-Lactide and 1,4-Dioxepan-2-one In a glove box, 7.60 grams (65.5 mmoles) of 1,4-dioxepan-2-one, sample 6-E, 38.0 grams (264 mmoles) of L-lactide, 21 µL (0.22 mmoles) of distilled DEG, and 39 µL (13 µmoles) of a 0.33M stannous octanoate solution in toluene were added into a flame dried, 100 mL round bottom flask equipped with a flame dried mechanical stirrer and vacuum port. The flask was attached to a vacuum manifold overnight to remove the toluene and other volatile compounds using a section of vacuum hose. Then, the reaction flask was transferred into a hood under an inert atmosphere. The flask was connected to a nitrogen gas line and immersed in an oil bath set at 185° C. for 24 hours and then at 110° C. for 24 hours. The melt viscosity increased slowly at 185° C. and eventually it became so high that mechanical stirring was only possible at very low speeds. Mechanical stirring was stopped when the temperature was reduced to 110° C. An inert atmosphere was maintained inside the reaction vessel throughout the polymerization. The statistically random copolymer was allowed to crystallize over the weekend and was isolated by freezing the flask in liquid nitrogen where the glass broke away. The copolymer was vacuum dried at 100° C. for 24 hours. 37.1 grams of copolymer were isolated (81% recovery). The inherent viscosity was 1.1 dL/g in HFIP at 25° C. (c=0.10 g/dL) after devolatization. The chemical composition of the statistically random copolymer was determined by 300 MHz proton NMR spectroscopy and was found to consist of 77.2 mole percent of PLA repeating units, 21.0 mole percent of PDP repeating units, 0.7 mole percent unreacted L-lactide, and 1.1 mole percent of residual 1,4-dioxepan-2-one. The glass transition temperature was 37° C. (observed only on the second heating scan) and the melting point was 118° C. as measured by DSC at a heating rate of 20° C. per minute under a nitrogen atmosphere.

The statistically random copolymer was spun and drawn into a fiber. The fiber was stretched on a rack and annealed at 60° C. for 6 hours. The annealed fiber (diameter 8.3 mils) had a straight tensile strength of 28 kpsi, a knot tensile strength of 22 kpsi, a Young's modulus of 250 kpsi, and an elongation to break of 110 percent. The in vitro BSR profile of this annealed fiber was measured in phosphate buffer pH 7.3 at 50° C. The annealed fiber retained 44 percent of its original straight tensile strength after four days and 27 percent after seven days, while a PLA control fiber retained 100 percent of its tensile strength after both four and seven days.

EXAMPLE 12

Preparation of a Segmented Block Copolymer from 1,4-Dioxanone and Poly[1,4-dioxepan-2-one]

In a glove box, 4.60 grams (39.7 mmoles of repeating units) of precipitated poly[1,4-dioxepan-2-one]- (I.V.=1.33 dL/g), 18.0 grams (176 mmoles) of 1,4-dioxanone, and 95.0 µL (31.7 mmoles) of a 0.33M stannous octanoate solution were added into a flame dried, 100 mL round bottom flask equipped with a flame dried mechanical stirrer and vacuum port. The flask was attached to a vacuum manifold to dry overnight using a section of vacuum hose. The reaction flask was then transferred into a hood under an inert atmosphere. The flask was connected to a nitrogen line and immersed in an oil bath set at 110° C. for eight hours. An inert atmosphere was maintained inside the reaction vessel throughout the polymerization. The poly[1,4-dioxepan-2-one]dissolved in the molten 1,4-dioxanone in about twenty five minutes with stirring. The segmented block copolymer was isolated by breaking the flask in liquid nitrogen. 16.6 grams were isloated. The product was vaccum dried at 70° C. for 24 hours and at 80° C. for 75 hours and lost 4.2 grams of unreacted monomers. The inherent viscosity was 1.7 dL/g before and after vacuum drying. The chemical composition of the segmented block copolymer was determined by 300 MHz proton NMR spectroscopy to consist of 84.8 mole percent of poly[1,4-dioxanone]repeating units and 15.2 mole percent of poly[1,4-dioxepan-2-one]repeating units. Glass transition temperatures were observed at −15° C. and 3° C., and the melting point was 102° C. as measured by DSC. A melting range of 93° C. to 106° C. was detected by hot stage optical microscopy.

The segmented block copolymer was spun and drawn into a fiber. The fiber was stretched on a rack and annealed at 80° C. for 6 hours. The annealed fiber (diameter 7.3 mils) had a straight tensile strength of 64 kpsi, a knot tensile strength of 42 kpsi, a Young's modulus of 81 kpsi, and an elongation to break of 54 percent. This annealed fiber had 72% BSR after four days and 57% BSR after seven days in phosphate buffer pH 7.27 at 50° C. This annealed fiber was also implanted intramuscularly in rats and its in vivo BSR profile measured: 71% BSR after seven days; 52% BSR after fourteen days; 36% after twenty one days.

EXAMPLE 13

Preparation of Statistically Random Copolymers of ε-Caprolactone and 1, 5, 8, 12-Tetraoxacyclotetradecane-7, 14-dione In a glove box, 9.00 grams (78.9 mmol) of distilled ε-caprolactone, 1.00 grams (4.31 mmol) of recrystallized 1,5,8,12-tetraoxacyclotetradecane-7,14-dione, 19 µL (0.20 mmol) of vacuum distilled diethylene glycol, and 50 µL (17 µmol) of a 0.33M stannous octoate solution were transferred into a clean, silanized, flame dried, 100 mL, round bottom flask. A flame dried vacuum adapter and a stirring assembly were fitted into the center ground glass joint. The stirring assembly consisted of a metal stirring rod and a teflon bearing. A vacuum hose was attached to the vaccum port and clamped off with a hemostat. The reaction vessel was moved into an exhaust hood. The hose was connected to a nitrogen gas line via a Firestone valve. The flask was immersed in an oil bath set a 190° C. An inert atmosphere was maintained throughout the reaction. The melt viscosity increased steadily and mechanical stirring was stopped after 75 minutes. After 24 hours at 190° C., the reaction vessel was removed from the oil bath and wrapped with aluminum foil. The polymer was allowed to stand and crystallize at room temperature overnight. The copolymer was melted and poured into a glass dish. The statistically random copolymer was shown to consist of 89.9 mole percent of poly[ε-caprolactone](PCL) repeating units and 10.1 mole percent of poly[1,4-dioxepan-2-one]repeating units by 300 MHz ¹H NMR spectroscopy. No residual ε-caprolactone or 1,5,8,12-tetraoxacyclotetradecane-7,14-dione was detected. Therefore,it appears that ε-caprolactone and 1,5,8,12--tetraoxacyclotetradecane-7,14-dione copolymerized to 100 percent conversion under these reaction conditions despite their differences in reactivity due to differences in ring size and strain. The inherent viscosity of the copolymer was measured in HFIP at 25° C. (c=0.10 g/dL) and found to be 1.1 dL/g.

Similar experimental results were obtained for 80:20, 70:30, and 60:40 (wt/wt) feed compositions of ε- caprolactone and 1,5,8,12-tetraoxacyclotetradecane-7,14-dione, respectively, and the copolymer characterization data is shown in Table VIII.

TABLE VIII
CHARACTERIZATION DATA[1] FOR RANDOM COPOLYMERS OF ε-CAPROLACTONE AND 1,5,8,12-TETRAOXACYCLOTETRADECANE-7,14-DIONE

| Sample | Copolymer Composition (mole %) | Inherent Viscosity (dL/g) | Melting Point (°C.) |
|---|---|---|---|
| 13-R | 89.9% PCL 10.1% PDP | 1.1 | 62 |
| 13-S | 80.1% PCL 19.9% PDP | 1.0 | 57 |
| 13-T | 69.8% PCL 30.2% PDP | 1.0 | 57 |
| 13-U | 61.0% PCL 39.0% PDP | 1.0 | 47 |

[1]The polymer compositions were determined by 300 MHz $^1$H NMR spectroscopy. The inherent viscosities were measured in HFIP at 25° C. [c = 0.10 dL/g]. The melting points were measured by DSC at 20° C./min under dry nitrogen gas.

EXAMPLE 14

Suture Coatings made from Statisticaly Random Copolymers of ε-Caprolactone and 1,5,8,12-Tetraoxacyclotetradecane-7,14-dione The four copolymers of ε-caprolactone and 1,5,8,12-tetraoxacyclotetradecane-7,14-dione described in Example 13 were evaluated as suture coatings on size 2/0 dyed VICRYL TM sutures. In qualitative screening tests, strands of 2/0 dyed VICRYL TM suture were passed through 10% (w/w) toluene solutions of each copolymer, dried, and evaluated for wet and dry tiedown performance. Copolymers 13-T and 12-U showed the most potential as braided suture coatings and were therefore evaluated more thoroughly.

600 Yards of annealed 2/0 dyed VICRYL TM braided suture were mechanically prepliabilized and ultrasonically scoured in acetone prior to coating. The braid was cut into three 200 yard segments. Then, using a small dip and dry coating apparatus, the braid was weighed, coated through a 10% (w/w) solution of the copolymer at a speed of 6 feet per minute, and dried in a heated tube between 110° F. and 120° F. The fiber was collected on a tared take up spool and reweighed to determine the amount of coating copolymer that was added onto the fiber. Table IX lists the results of the coating operations for copolymers 12-C and 12-D.

TABLE IX
COATING LEVELS ON VICRYL TM SUTURE

| COATED SUTURE | COATING COPOLYMER | COATING WEIGHT PERCENT[1] |
|---|---|---|
| 14-V | 13-T | 3.0 |
| 14-W | 12-U | 2.8 |

[1]The coating weight percent was calculated as the amount of coating copolymer added on to the suture; hence, it was expressed in terms of the weight percent increase in the weight of the fiber.

After coating, the fiber was wound on a rack and cut into 30 inch segments. The resulting bundles of sutures were wound and packaged in paper folders. The paper folders of suture along with the appropriate snap out forms, 12C forms, and labels were foil wrapped, primarily E/O sterilized, overwrapped, secondarily E/O sterilized, and placed in a hot room at 50° C. for four days. These sterile sutures were tested for their tensile properties, tiedown characteristics, and handling in comparison to uncoated 2/0 dyed VICRYL TM suture. The results of these tests are shown in Table X.

TABLE X
PHYSICAL PROPERTIES OF THE COATED SUTURES

| PROPERTY | Uncoated VICRYL TM | Coated VICRYL TM 14-V | Coated VICRYL TM 14-W |
|---|---|---|---|
| Diameter (mils) | 13.0 | 12.8 | 12.8 |
| Straigth Tensile Strength (kpsi) | 117 | 116 | 116 |
| Elongation (%) | 20.7 | 19.6 | 20.5 |
| Dry Knot Tensile Strength (kpsi) | 61.3 | 68.5 | 70.9 |
| Wet Knot Tensile Strength (kpsi) | 60.3 | 72.3 | 72.2 |
| Tissue Drag (gram) | 133.2 | 57.4 | 52.9 |
| Dry Roughness (grams) | 429 | 132 | 136 |
| Wet Roughness (grams) | 489 | 137 | 149 |
| Wet Knot Security (lbs) | 7.93 | 9.15 | 8.76 |
| Wet Knot Security (# of throws) | 2 | 5 | 5 |
| Gurley Pliability Test (milligrams) | 2.92 | 4.54 | 3.40 |

When compared to uncoated 2/0 dyed VICRYL TM suture, both coated sutures had superior physical properties. In particular, the dry knot tensile strength increased an average of 13.7 percent ("average" means the average improvement of the two coated sutures); the wet knot tensile strength increased an average of 19.8 percent; the tissue drag was reduced by an average of 58.6 percent; dry roughness tiedown was 68.7 percent smoother on average; wet roughness tiedown was 70.7 percent smoother on average; and the absolute wet knot strength increased an average of 14.4 percent. The dry straight tensile strength and tactile smoothness of the uncoated and coated sutures were identical. Only the wet knot security of the coated sutures decreased in comparison to the uncoated VICRYL TM which is not uncommon for coated braided sutures. The uncoated suture has a rougher surface and therefore requires fewer knots (2 versus 5 in this case) for a secure hold. The coated sutures were also stiffer (Gurley) than the uncoated VICRYL TM by an average of 35.9 percent. The coated sutures can be made more pliable, if necessary, by employing a coating copolymer of lower molecular weight.

We claim:

1. A copolymer comprising a first repeating unit of the chemical formula:

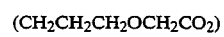

(CH$_2$CH$_2$CH$_2$OCH$_2$CO$_2$)

and a second repeating unit having a chemical formula selected from the group consisting of:

($CHRCO_2$), ($[CH_2]_5CO_2$), ($CH_2CH_2OCH_2CO_2$), ($CH_2CH_2CH_2OCO_2$), and combinations of two or more thereof wherein R is a hydrogen atom or a methyl group and the first repeating unit is less than 45 weight percent of the total weight of the copolymer wherein the copolymer is selected from the group consisting of:
 a) a copolymer comprising the reaction product of a prepolymer of the first repeating unit the remainder of the copolymer being the second repeating unit;
 b) a random copolymer comprising the first repeating unit and the second repeating unit;
 c) a copolymer comprising the reaction product of a prepolymer containing the second repeating unit and the remainder of the copolymer being the first repeating unit;
 d) a copolymer comprising the reaction product of a prepolymer containing less than 45 weight percent of the first repeating unit and greater than 55 weight percent of the second repeating unit in the prepolymer and the remainder of the copolymer being the second repeating unit.

2. The copolymer of claim 1 wherein the copolymer is the reaction product of a prepolymer of the first repeating unit and the remainder of the copolymer is the second repeating unit.

3. The copolymer of claim 1 wherein the copolymer is the random copolymer of the first repeating unit and the second repeating unit.

4. The copolymer of claim 1 wherein the copolymer comprises the reaction product of a prepolymer containing the second repeating unit and the remainder of the copolymer being the first repeating unit.

5. The copolymer of claim 1 wherein the copolymer is the reaction product of a prepolymer containing less than 45 weight percent of the first repeating unit and greater than 55 weight percent of the second repeating unit in the prepolymer and the remainder of the copolymer being the second repeating unit.

6. The copolymer of claim 3 wherein the second repeating unit is of the chemical formula:

($[CH_2]_5CO_2$).

7. The copolymer of claim 4 wherein additionally present with the first repeating unit in the remainder of the copolymer is the second repeating unit.

8. A surgical device comprising a copolymer composed of a first repeating unit of the chemical formula:

($CH_2CH_2CH_2OCH_2CO_2$)

and a second repeating unit having a chemical formula selected from the group consisting of:

($CHRCO_2$), ($[CH_2]_5CO_2$), ($CH_2CH_2OCH_2CO_2$), ($CH_2CH_2CH_2OCO_2$), and combinations of two or more thereof wherein R is a hydrogen atom or a methyl group and the first repeating unit is less than 45 weight percent of the total weight of the copolymer wherein the copolymer is selected from the group consisting of:
 a) a copolymer comprising the reaction product of a prepolymer of the first repeating unit the remainder of the copolymer being the second repeating unit;
 b) a random copolymer comprising the first repeating unit and the second repeating unit;
 c) a copolymer comprising the reaction product of a prepolymer containing the second repeating unit and the remainder of the copolymer being the first repeating unit;
 d) a copolymer comprising the reaction product of a prepolymer containing less than 45 weight percent of the first repeating unit and greater than 55 weight percent of the second repeating unit in the prepolymer and the remainder of the copolymer being the second repeating unit.

9. The surgical device of claim 8 wherein the surgical device is selected from the group consisting of sutures, ligaments, ribbons, pins, screws, clamps, plates, films, medical dressings, hernia patches, gauze, meshes, fabrics, felts, sponges, surgical staples, hemostatic clips, suture knot clips, hooks, buttons, snaps, bone substitutes and vascular implants.

10. The surgical device of claim 9 wherein the copolymer is the reaction product of a prepolymer of the first repeating unit and the remainder of the copolymer is the second repeating unit.

11. The surgical device of claim 9 wherein the copolymer is a random copolymer comprising the first repeating unit and the second repeating unit.

12. The surgical device of claim 9 wherein the copolymer is the reaction product of a prepolymer containing the second repeating unit the remainder of the copolymer being the first repeating unit.

13. The surgical device of claim 9 wherein the copolymer is a copolymer comprising the reaction product of a prepolymer containing less than 45 weight percent of the first repeating unit and greater than 55 weight percent of the second repeating unit in the prepolymer; the remainder of the copolymer being the second repeating unit.

14. The surgical device of claim 8 wherein the surgical device is a suture.

15. The surgical device of claim 9 wherein the surgical device is a suture.

16. The surgical device of claim 15 wherein the suture is attached to at least one needle.

17. The surgical device of claim 12 wherein additionally present with the first repeating unit in the remainder of the copolymer is the second repeating unit.

18. A suture coated with a copolymer composed of a first repeating unit of the chemical formula:

($CH_2CH_2CH_2OCH_2CO_2$)

and a second repeating unit having a chemical formula selected from the group consisting of:

($CHRCO_2$), $([CH_2]_5CO_2)$, $(CH_2CH_2OCH_2CO_2)$, $(CH_2CH_2CH_2OCO_2)$, and combinations of two or more thereof wherein R is a hydrogen atom or a methyl group and the first repeating unit is less than 45 weight percent of the total weight of the copolymer wherein the copolymer is selected from the group consisting of:
   a) a copolymer comprising the reaction product of a prepolymer of the first repeating unit the remainder of the copolymer being the second repeating unit;
   b) a random copolymer comprising the first repeating unit and the second repeating unit;
   c) a copolymer comprising the reaction product of a prepolymer containing the second repeating unit and the remainder of the copolymer being the first repeating unit;
   d) a copolymer comprising the reaction product of a prepolymer containing less than 45 weight percent of the first repeating unit and greater than 55 weight percent of the second repeating unit in the prepolymer and the remainder of the copolymer being the second repeating unit.

19. The coated suture of claim 18 wherein the copolymer is the reaction product of a prepolymer of the first repeating unit and the remainder of the copolymer is the second repeating unit.

20. The coated suture of claim 18 wherein the copolymer is a random copolymer comprising the first repeating unit and the second repeating unit.

21. The coated suture of claim 18 wherein the copolymer is the reaction product of a prepolymer containing the second repeating unit and the remainder of the copolymer being the first repeating unit.

22. The coated suture of claim 18 wherein the copolymer is a copolymer comprising the reaction product of a prepolymer containing less than 45 weight percent of the first repeating unit and greater than 55 weight percent of the second repeating unit in the prepolymer; the remainder of the copolymer being the second repeating unit.

23. The copolymer of claim 20 wherein the second repeating unit is of the formula:

$([CH_2]_5CO_2)$.

24. The coated suture of claim 18 wherein the suture is attached to at least one needle.

25. The copolymer of claim 1 wherein the first repeating unit is in the range of from about 1 to about 40 weight percent of the total weight percent of the copolymer.

26. A copolymer comprising a first repeating unit of the chemical formula:

$(CH_2CH_2CH_2OCH_2CO_2)$ and a second repeating unit has the chemical formula of:

$([CH_2]_5CO_2)$, wherein the first repeating unit is less than 45 weight percent of the total weight of the copolymer wherein the copolymer is selected from the group consisting of:
   a) a copolymer comprising the reaction product of a prepolymer of the first repeating unit the remainder of the copolymer being the second repeating unit;
   b) a random copolymer comprising the first repeating unit and the second repeating unit;
   c) a copolymer comprising the reaction product of a prepolymer containing the second repeating unit and the remainder of the copolymer being the first repeating unit;
   d) a copolymer comprising the reaction product of a prepolymer containing less than 45 weight percent of the first repeating unit and greater than 55 weight percent of the second repeating unit in the prepolymer and the remainder of the copolymer being the second repeating unit.

* * * * *